United States Patent
Morikazu et al.

(10) Patent No.: US 9,174,305 B2
(45) Date of Patent: Nov. 3, 2015

(54) LASER PROCESSING APPARATUS INCLUDING PLASMA DETECTING MEANS

(71) Applicant: Disco Corporation, Tokyo (JP)

(72) Inventors: Hiroshi Morikazu, Tokyo (JP); Yoko Nishino, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 432 days.

(21) Appl. No.: 13/649,363

(22) Filed: Oct. 11, 2012

(65) Prior Publication Data

US 2013/0092669 A1 Apr. 18, 2013

(30) Foreign Application Priority Data

Oct. 18, 2011 (JP) .................... 2011-228971

(51) Int. Cl.
| | |
|---|---|
| B23K 26/14 | (2014.01) |
| B23K 26/08 | (2014.01) |
| B23K 26/03 | (2006.01) |
| H01L 21/67 | (2006.01) |
| G01N 21/71 | (2006.01) |
| G01N 21/73 | (2006.01) |
| H01L 21/66 | (2006.01) |
| B23K 26/40 | (2014.01) |
| H01L 33/00 | (2010.01) |

(52) U.S. Cl.
CPC .......... B23K 26/032 (2013.01); B23K 26/0853 (2013.01); B23K 26/409 (2013.01); G01N 21/718 (2013.01); G01N 21/73 (2013.01); H01L 21/67092 (2013.01); H01L 21/67253 (2013.01); H01L 22/26 (2013.01); H01L 33/0095 (2013.01); H01L 33/007 (2013.01)

(58) Field of Classification Search
CPC ............ B23K 26/00–26/106; B23K 26/409; H01L 33/005–33/0095; H01L 21/67092; G01N 21/73
USPC .......................... 219/121.6–121.83
See application file for complete search history.

(56) References Cited

U.S. PATENT DOCUMENTS

| | | | | |
|---|---|---|---|---|
| 5,847,825 | A | * 12/1998 | Alexander | ............ 356/318 |
| 6,791,057 | B1 | * 9/2004 | Kratzsch et al. | ....... 219/121.63 |
| 7,696,523 | B2 | * 4/2010 | Jang et al. | ................ 257/98 |
| 2008/0003708 | A1 | * 1/2008 | Hoshino et al. | ............ 438/33 |

FOREIGN PATENT DOCUMENTS

| | | |
|---|---|---|
| JP | 10-305420 | 11/1998 |
| JP | 2005-516415 | 6/2005 |
| JP | 2007-284288 | 11/2007 |
| JP | 2007-534164 | 11/2007 |
| JP | 2011-151400 | 8/2011 |
| WO | WO 03/065420 | 8/2003 |
| WO | WO 2005/094320 | 10/2005 |

* cited by examiner

*Primary Examiner* — Sang Y Paik

(74) *Attorney, Agent, or Firm* — Greer Burns & Crain, Ltd.

(57) ABSTRACT

A laser processing apparatus removes a sapphire substrate from an optical device wafer configured by forming an optical device layer on the front side of the sapphire substrate through a buffer layer. A chuck table holds the optical device wafer. A pulsed laser beam is applied to the optical device wafer to break the buffer layer, and the light intensity of plasma light produced in the buffer layer by the application of the pulsed laser beam is detected and displayed. The light intensity of a predetermined wavelength region of the plasma light generated from a substance forming the buffer layer is detected.

2 Claims, 10 Drawing Sheets

LASER PROCESSING APPARATUS INCLUDING PLASMA DETECTING MEANS

BACKGROUND OF THE INVENTION

1. Field of the Invention

The present invention relates to a laser processing apparatus including plasma detecting means.

2. Description of the Related Art

In an optical device fabrication process, an optical device layer composed of an n-type semiconductor layer and a p-type semiconductor layer is formed on the front side of a substantially disk-shaped epitaxy substrate such as a sapphire substrate through a buffer layer, and this optical device layer is partitioned by a plurality of crossing streets into a plurality of regions where a plurality of optical devices such as light emitting diodes and laser diodes are respectively formed, thus constituting an optical device wafer. The optical device wafer is divided along the streets to thereby obtain the individual optical devices (see Japanese Patent Laid-open No. Hei 10-305420, for example).

Further, as a technique for improving the luminance of an optical device, a manufacturing method called lift-off is disclosed in Japanese Unexamined Patent Application Publication 2005-516415. In an optical device wafer, an optical device layer composed of an n-type semiconductor layer and a p-type semiconductor layer is formed on the front side of an epitaxy substrate such as a sapphire substrate through a buffer layer. The above-mentioned method called lift-off includes the steps of bonding the optical device layer of the optical device wafer through a bonding metal layer formed of gold (Au), platinum (Pt), chromium (Cr), indium (In), or palladium (Pd) to a transfer substrate formed of molybdenum (Mo), copper (Cu), or silicon (Si) and next applying a laser beam from the back side of the epitaxy substrate to the buffer layer to thereby peel off the epitaxy substrate, thus transferring the optical device layer to the transfer substrate.

SUMMARY OF THE INVENTION

However, the thickness of the buffer layer is as small as about 1 μm and it is formed of gallium nitride that is the same material as that of the optical device layer composed of the n-type semiconductor layer and the p-type semiconductor layer. Accordingly, it is difficult to reliably break only the buffer layer by applying the laser beam thereto.

It is therefore an object of the present invention to provide a laser processing apparatus including plasma detecting means which can be suitably used to peel off the epitaxy substrate from the optical device layer by applying the laser beam to the buffer layer from the back side of the epitaxy substrate.

In accordance with an aspect of the present invention, there is provided a laser processing apparatus for removing a sapphire substrate from an optical device wafer configured by forming an optical device layer on the front side of the sapphire substrate through a buffer layer, the laser processing apparatus including a chuck table for holding the optical device wafer; laser beam applying means for applying a pulsed laser beam to the optical device wafer held on the chuck table to break the buffer layer; plasma detecting means for detecting the light intensity of plasma light produced in the buffer layer by the application of the pulsed laser beam from the laser beam applying means to the optical device wafer, the plasma detecting means detecting the light intensity of a predetermined wavelength region of the plasma light generated from a substance forming the buffer layer; and displaying means for displaying the light intensity of the plasma light detected by the plasma detecting means.

Preferably, the plasma detecting means includes a dichroic mirror for transmitting the pulsed laser beam applied from the laser beam applying means and reflecting the plasma light produced in the buffer layer, a band-pass filter for passing the predetermined wavelength region of the plasma light generated from the substance forming the buffer layer after the plasma light is reflected by the dichroic mirror, and a photodetector for detecting the light intensity of the plasma light passed through the band-pass filter; the result of detection by the photodetector being displayed by the displaying means.

The laser processing apparatus of the present invention includes the plasma detecting means for detecting the light intensity of the plasma light produced by the application of the laser beam to the buffer layer. Accordingly, by controlling power adjusting means included in the laser beam applying means according to the information displayed by the displaying means, a proper power of the laser beam for breaking only the buffer layer can be set.

The above and other objects, features and advantages of the present invention and the manner of realizing them will become more apparent, and the invention itself will best be understood from a study of the following description and appended claims with reference to the attached drawings showing some preferred embodiments of the invention.

DETAILED DESCRIPTION OF THE PREFERRED EMBODIMENT

Figure 1:
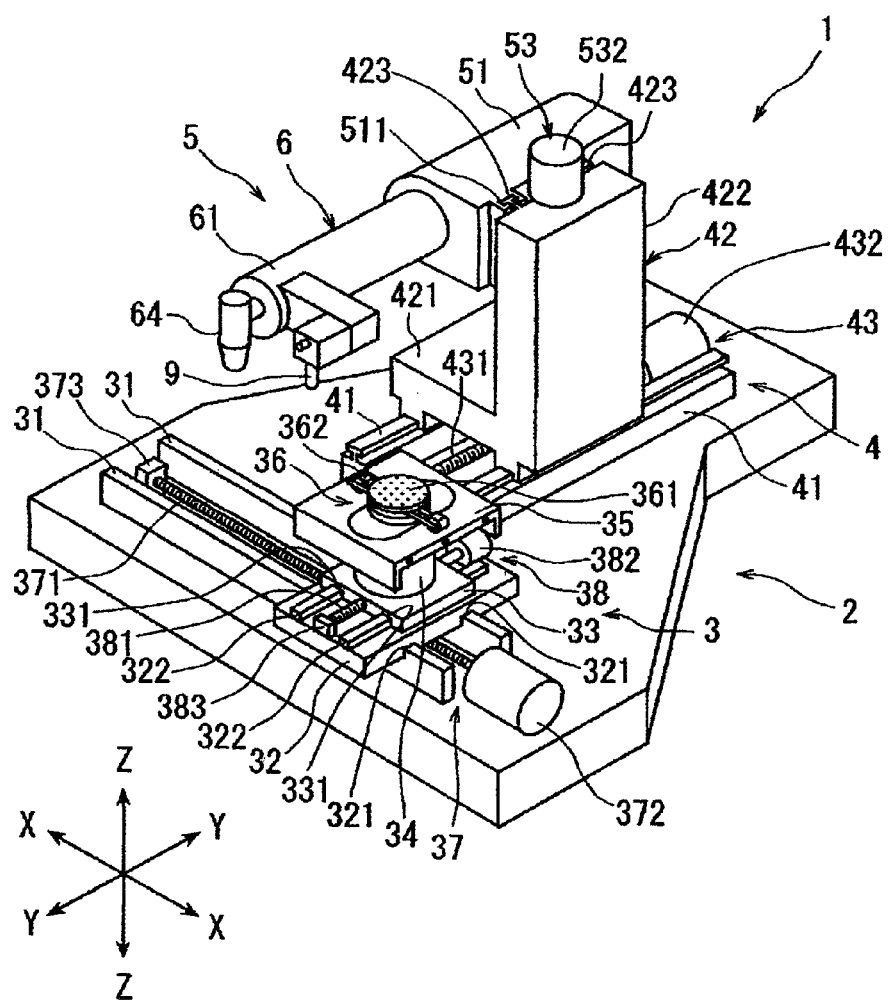
FIG. 1 is a perspective view of a laser processing apparatus according to a preferred embodiment of the present invention.

A preferred embodiment of the laser beam power setting method and the laser processing apparatus according to the present invention will now be described in detail with reference to the attached drawings. FIG. 1 is a perspective view of a laser processing apparatus 1 according to a preferred embodiment of the present invention for performing the laser beam power setting method. The laser processing apparatus 1 shown in FIG. 1 includes a stationary base 2, a chuck table mechanism 3 for holding a workpiece, the chuck table mechanism 3 being provided on the stationary base 2 so as to be movable in a feeding direction (X direction) shown by an arrow X, a laser beam applying unit supporting mechanism 4 provided on the stationary base 2 so as to be movable in an indexing direction (Y direction) shown by an arrow Y perpendicular to the X direction, and a laser beam applying unit 5 provided on the laser beam applying unit supporting mechanism 4 so as to be movable in a focal position adjusting direction (Z direction) shown by an arrow Z.

The chuck table mechanism 3 includes a pair of guide rails 31 provided on the stationary base 2 so as to extend parallel to each other in the X direction, a first slide block 32 provided on the guide rails 31 so as to be movable in the X direction, a second slide block 33 provided on the first slide block 32 so as to be movable in the Y direction, a cover table 35 supported by a cylindrical member 34 standing on the second slide block 33, and a chuck table 36 as workpiece holding means. The chuck table 36 has a vacuum chuck 361 formed of a porous material. A workpiece such as a disk-shaped semiconductor wafer is adapted to be held under suction on the upper surface (holding surface) of the vacuum chuck 361 by operating suction means (not shown). The chuck table 36 is rotatable by a pulse motor (not shown) provided in the cylindrical member 34. Further, the chuck table 36 is provided with clamps 362 for fixing an annular frame to be hereinafter described.

The lower surface of the first slide block 32 is formed with a pair of guided grooves 321 for slidably engaging the pair of guide rails 31 mentioned above. A pair of guide rails 322 are provided on the upper surface of the first slide block 32 so as to extend parallel to each other in the Y direction. Accordingly, the first slide block 32 is movable in the X direction along the guide rails 31 by the slidable engagement of the guided grooves 321 with the pair of guide rails 31. The chuck table mechanism 3 further includes feeding means 37 for moving the first slide block 32 in the X direction along the guide rails 31. The feeding means 37 includes an externally threaded rod 371 extending parallel to the guide rails 31 so as to be interposed therebetween and a pulse motor 372 as a drive source for rotationally driving the externally threaded rod 371. The externally threaded rod 371 is rotatably supported at one end thereof to a bearing block 373 fixed to the stationary base 2 and is connected at the other end to the output shaft of the pulse motor 372 so as to receive the torque thereof. The externally threaded rod 371 is engaged with a tapped through hole formed in an internally threaded block (not shown) projecting from the lower surface of the first slide block 32 at a central portion thereof. Accordingly, the first slide block 32 is moved in the X direction along the guide rails 31 by operating the pulse motor 372 to normally or reversely rotate the externally threaded rod 371.

The lower surface of the second slide block 33 is formed with a pair of guided grooves 331 for slidably engaging the pair of guide rails 322 provided on the upper surface of the first slide block 32 as mentioned above. Accordingly, the second slide block 33 is movable in the Y direction along the guide rails 322 by the slidable engagement of the guided grooves 331 with the guide rails 322. The chuck table mechanism 3 further includes first indexing means 38 for moving the second slide block 33 in the Y direction along the guide rails 322. The first indexing means 38 includes an externally threaded rod 381 extending parallel to the guide rails 322 so as to be interposed therebetween and a pulse motor 382 as a drive source for rotationally driving the externally threaded rod 381. The externally threaded rod 381 is rotatably supported at one end thereof to a bearing block 383 fixed to the upper surface of the first slide block 32 and is connected at the other end to the output shaft of the pulse motor 382 so as to receive the torque thereof. The externally threaded rod 381 is engaged with a tapped through hole formed in an internally threaded block (not shown) projecting from the lower surface of the second slide block 33 at a central portion thereof. Accordingly, the second slide block 33 is moved in the Y direction along the guide rails 322 by operating the pulse motor 382 to normally or reversely rotate the externally threaded rod 381.

The laser beam applying unit supporting mechanism 4 includes a pair of guide rails 41 provided on the stationary base 2 so as to extend parallel to each other in the Y direction and a movable support base 42 provided on the guide rails 41 so as to be movable in the Y direction. The movable support base 42 is composed of a horizontal portion 421 slidably supported to the guide rails 41 and a vertical portion 422 extending vertically upward from the upper surface of the horizontal portion 421. Further, a pair of guide rails 423 are provided on one side surface of the vertical portion 422 so as to extend parallel to each other in the Z direction. The laser beam applying unit supporting mechanism 4 further includes second indexing means 43 for moving the movable support base 42 in the Y direction along the guide rails 41. The second indexing means 43 includes an externally threaded rod 431 extending parallel to the guide rails 41 so as to be interposed therebetween and a pulse motor 432 as a drive source for rotationally driving the externally threaded rod 431. The externally threaded rod 431 is rotatably supported at one end thereof to a bearing block (not shown) fixed to the stationary base 2 and is connected at the other end to the output shaft of the pulse motor 432 so as to receive the torque thereof. The externally threaded rod 431 is engaged with a tapped through hole formed in an internally threaded block (not shown) projecting from the lower surface of the horizontal portion 421 at a central portion thereof. Accordingly, the movable support base 42 is moved in the Y direction along the guide rails 41 by operating the pulse motor 432 to normally or reversely rotate the externally threaded rod 431.

The laser beam applying unit 5 includes a unit holder 51 and laser beam applying means 6 mounted to the unit holder 51. The unit holder 51 is formed with a pair of guided grooves 511 for slidably engaging the pair of guide rails 423 provided on the vertical portion 422 of the movable support base 42. Accordingly, the unit holder 51 is supported to the movable support base 42 so as to be movable in the Z direction by the slidable engagement of the guided grooves 511 with the guide rails 423.

The laser beam applying unit 5 further includes focal position adjusting means 53 for moving the unit holder 51 along the guide rails 423 in the Z direction. The focal position adjusting means 53 includes an externally threaded rod (not shown) extending parallel to the guide rails 423 so as to be interposed therebetween and a pulse motor 532 as a drive source for rotationally driving this externally threaded rod. Accordingly, the unit holder 51 and the laser beam applying means 6 are moved in the Z direction along the guide rails 423 by operating the pulse motor 532 to normally or reversely rotate this externally threaded rod. In this preferred embodiment, when the pulse motor 532 is normally operated, the laser beam applying means 6 is moved upward, whereas when the pulse motor 532 is reversely operated, the laser beam applying means 6 is moved downward.

Figure 2:
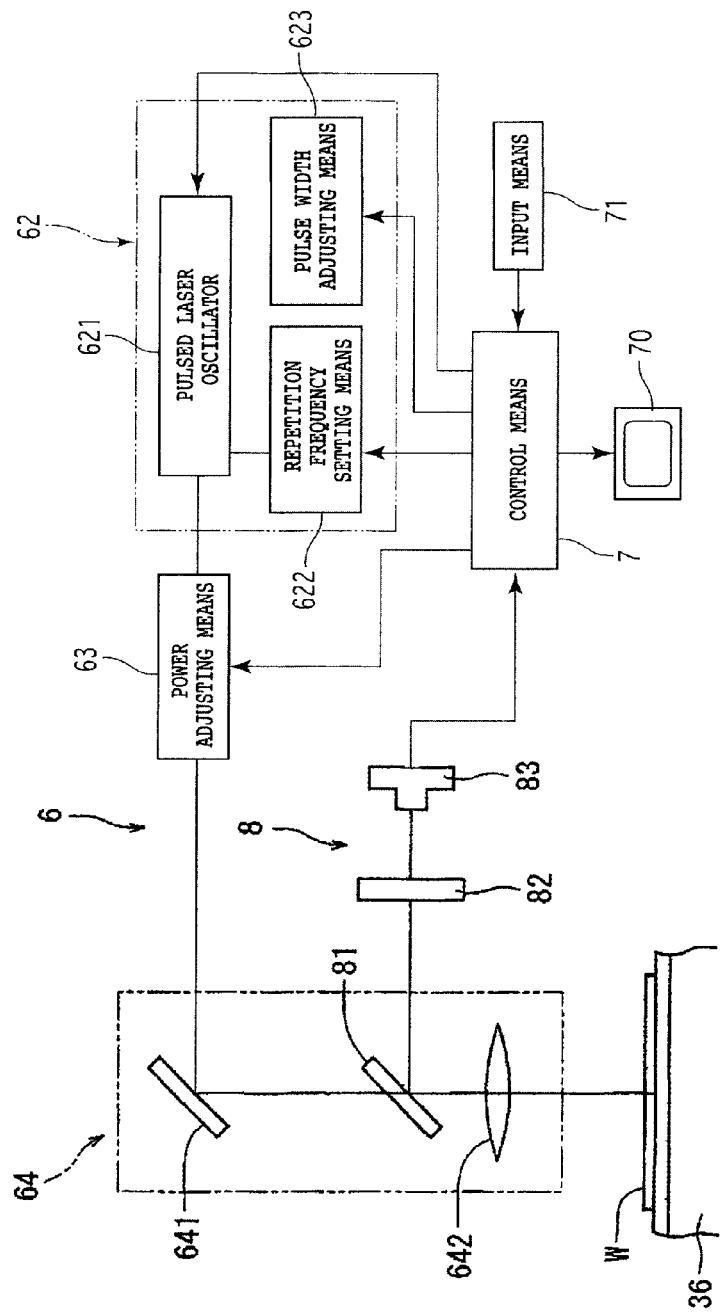
FIG. 2 is a block diagram showing the configuration of laser beam applying means and plasma detecting means included in the laser processing apparatus shown in FIG. 1.

The laser beam applying means 6 includes a cylindrical casing 61 fixed to the unit holder 51 so as to extend in a substantially horizontal direction. The configuration of the laser beam applying means 6 will now be described with reference to FIG. 2. The laser beam applying means 6 includes pulsed laser beam oscillating means 62 provided in the casing 61, power adjusting means 63 for adjusting the power of a pulsed laser beam oscillated by the pulsed laser beam oscillating means 62, and focusing means 64 for applying the pulsed laser beam whose power has been adjusted by the power adjusting means 63 to a workpiece W held on the holding surface of the chuck table 36.

The pulsed laser beam oscillating means 62 is composed of a pulsed laser oscillator 621 for oscillating a pulsed laser beam having a wavelength of 257 nm, for example, repetition frequency setting means 622 for setting the repetition frequency of the pulsed laser beam to be oscillated by the pulsed laser oscillator 621, and pulse width adjusting means 623 for adjusting the pulse width of the pulsed laser beam to be oscillated by the pulsed laser oscillator 621. The power adjusting means 63 functions to adjust the power of the pulsed laser beam oscillated by the pulsed laser beam oscillating means 62 to a predetermined power. All of the pulsed laser oscillator 621, the repetition frequency setting means 622, and the pulse width adjusting means 623 of the pulsed laser beam oscillating means 62 and the power adjusting means 63 are controlled by control means 7.

The focusing means 64 includes a direction changing mirror 641 for changing the traveling direction of the pulsed laser beam oscillated by the pulsed laser beam oscillating means 62 and adjusted in power by the power adjusting means 63 toward the holding surface of the chuck table 36 and a focusing lens 642 for focusing the pulsed laser beam whose traveling direction has been changed by the direction changing mirror 641 and applying the pulsed laser beam to the workpiece W held on the chuck table 36. The focusing means 64 is mounted on the front end of the casing 61 as shown in FIG. 1.

Referring again to FIG. 2, the laser processing apparatus 1 further includes plasma detecting means 8 for detecting the light intensity of plasma generated by the application of the pulsed laser beam oscillated by the pulsed laser beam oscillating means 62 and adjusted in power by the power adjusting means 63 to the workpiece W held on the chuck table 36. The plasma detecting means 8 includes a dichroic mirror 81 provided between the direction changing mirror 641 and the focusing lens 642 for reflecting the plasma generated by the application of the pulsed laser beam to the workpiece W held on the chuck table 36, a band-pass filter 82 for passing light having a predetermined wavelength region (e.g., 400 to 420 nm in this preferred embodiment) in the plasma reflected by the dichroic mirror 81, and a photodetector 83 for detecting the plasma light passed through the band-pass filter 82.

The dichroic mirror 81 transmits the pulsed laser beam having a wavelength of 257 nm oscillated by the pulsed laser beam oscillating means 62 and changed in traveling direction by the direction changing mirror 641, but reflects the plasma generated by the application of the pulsed laser beam to the workpiece W held on the chuck table 36 toward the band-pass filter 82. The band-pass filter 82 transmits light having a wavelength region of 410±10 nm (400 to 420 nm), where 410 nm is the wavelength of the plasma for gallium (Ga), and blocks light having the other wavelength regions. The photodetector 83 detects the plasma passed through the band-pass filter 82 and sends a detection signal as a light intensity signal to the control means 7. The control means 7 outputs to display means 70 the light intensity of the plasma in the wavelength region of 400 to 420 nm according to the light intensity signal sent from the photodetector 83. Processing conditions or the like are input from input means 71 to the control means 7.

Another preferred embodiment of the plasma detecting means 8 will now be described with reference to FIG. 3.

Figure 3:
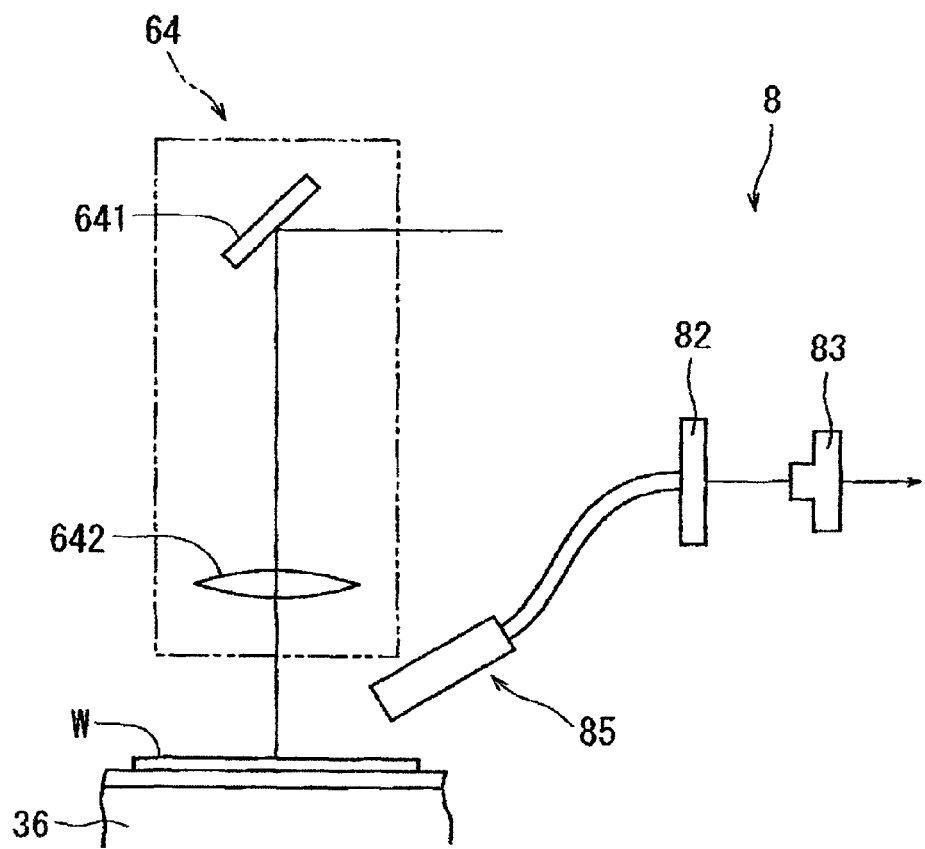
FIG. 3 is a block diagram showing another preferred embodiment of the plasma detecting means included in the laser processing apparatus shown in FIG. 1.

The plasma detecting means 8 shown in FIG. 3 includes plasma sensing means 85 provided adjacent to the focusing means 64 of the laser beam applying means 6 for sensing the plasma generated by the application of the pulsed laser beam from the focusing means 64 to the workpiece W held on the chuck table 36. The plasma sensed by the plasma sensing means 85 is guided through the band-pass filter 82 to the photodetector 83.

Referring back to FIG. 1, the laser processing apparatus 1 further includes alignment means 9 provided at the front end portion of the casing 61 for imaging a subject area to be laser-processed by the laser beam applying means 6. The alignment means 9 is configured by optical means including a microscope and a CCD camera. An image signal output from the alignment means 9 is transmitted to the control means 7.

Figure 4A:
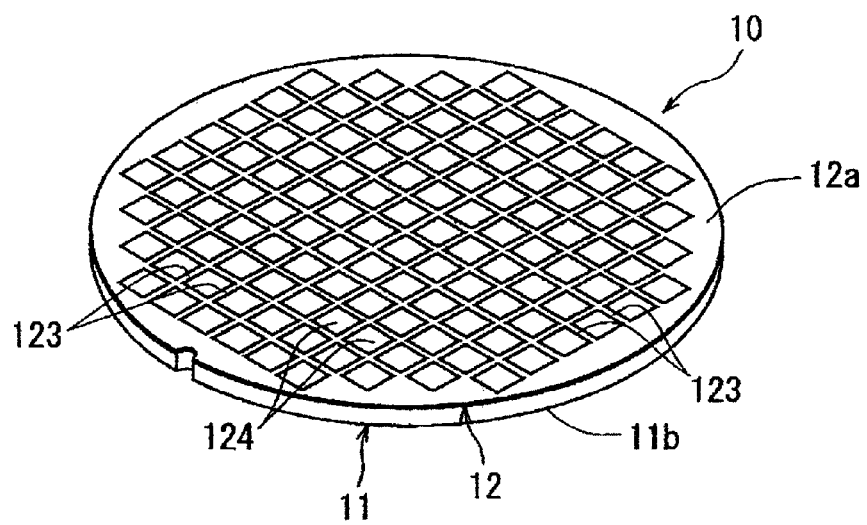
FIG. 4A is a perspective view of an optical device wafer to be used in a laser beam power setting method according to the present invention.
Figure 4B:
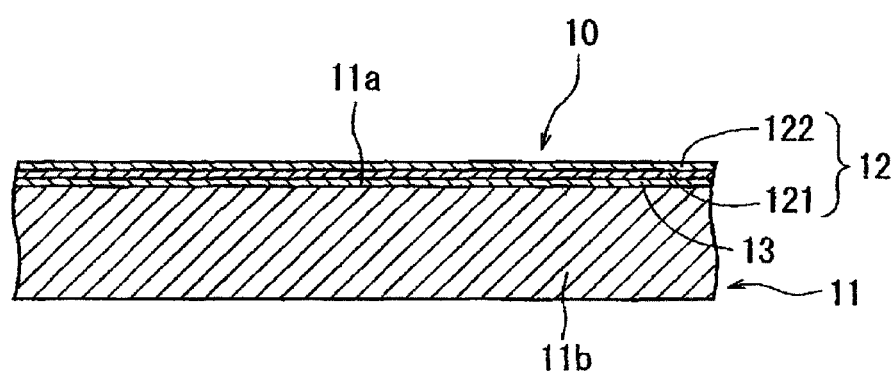
FIG. 4B is an enlarged sectional view of an essential part of the optical device wafer shown in FIG. 4A.

The operation of the laser processing apparatus 1 configured above will now be described. FIG. 4A is a perspective view of an optical device wafer 10 to be processed by the laser processing apparatus 1, and FIG. 4B is an enlarged sectional view of an essential part of the optical device wafer 10 shown in FIG. 4A. The optical device wafer 10 shown in FIGS. 4A and 4B is formed by epitaxial growth of an optical device layer 12 on the front side 11a of a circular epitaxy substrate 11. The epitaxy substrate 11 is formed from a sapphire substrate. The epitaxy substrate 11 has a diameter of 50 mm and a thickness of 600 μm, for example. The optical device layer 12 is composed of an n-type gallium nitride semiconductor layer 121 and a p-type gallium nitride semiconductor layer 122. In forming the optical device layer 12 composed of the n-type gallium nitride semiconductor layer 121 and the p-type gallium nitride semiconductor layer 122 on the front side 11a of the epitaxy substrate 11 by epitaxial growth, a buffer layer 13 of gallium nitride (GaN) is formed between the front side 11a of the epitaxy substrate 11 and the n-type gallium nitride semiconductor layer 121 forming the optical device layer 12. The buffer layer 13 has a thickness of 1 μm, for example, and the optical device layer 12 has a thickness of 10 μm, for example. As shown in FIG. 4A, the optical device layer 12 is partitioned by a plurality of crossing streets 123 to define a plurality of regions where a plurality of optical devices 124 are respectively formed.

Figure 5A:
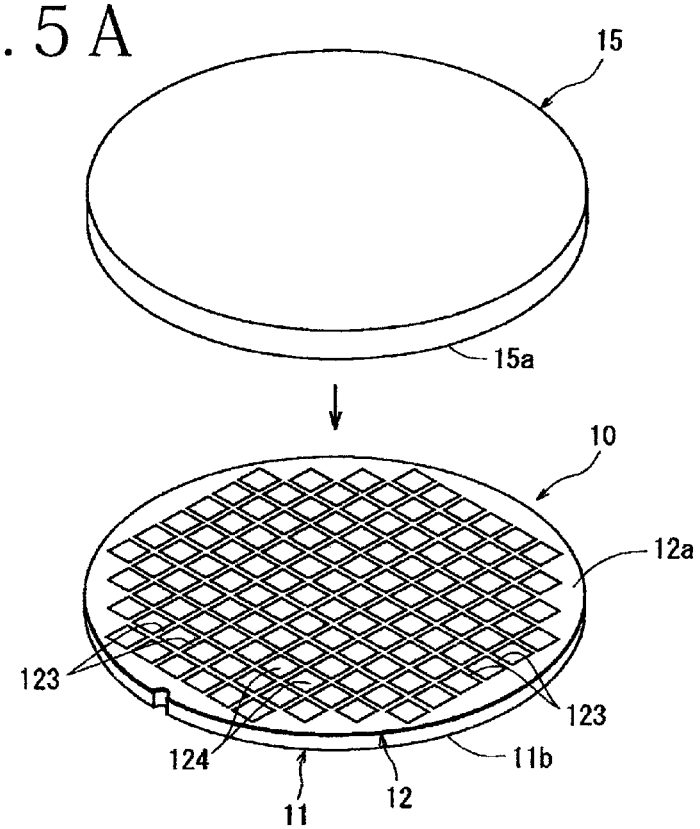
FIG. 5A is a perspective view for illustrating a transfer substrate bonding step of bonding a transfer substrate to the front side of an optical device layer constituting the optical device wafer shown in FIG. 4A.
Figure 5B:
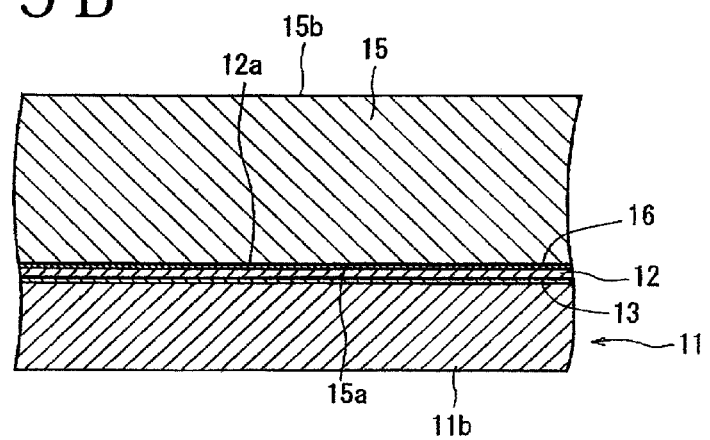
FIG. 5B is an enlarged sectional view of an essential part of the unit of the optical device wafer and the transfer substrate bonded together by the transfer substrate bonding step shown in FIG. 5A.

To peel off the epitaxy substrate 11 from the optical device layer 12 in the optical device wafer 10 and transfer the optical device layer 12 to a transfer substrate, a transfer substrate bonding step is first performed in such a manner that the transfer substrate is bonded to the front side 12a of the optical device layer 12. More specifically, as shown in FIGS. 5A and 5B, a transfer substrate 15 having a thickness of 1 mm, for example, is bonded through a bonding metal layer 16 to the front side 12a of the optical device layer 12 formed on the front side 11a of the epitaxy substrate 11 constituting the optical device wafer 10. In this preferred embodiment, the transfer substrate 15 is formed of copper, and the bonding metal layer 16 is formed of tin. The transfer substrate 15 may be formed of molybdenum (Mo) or silicon (Si), for example, and the bonding metal layer 16 may be formed of gold (Au), platinum (Pt), chromium (Cr), indium (In), or palladium (Pd), for example, as a bonding metal. This transfer substrate bonding step is performed in the following manner. The bonding metal mentioned above is deposited by evaporation to the front side 12a of the optical device layer 12 formed on the front side 11a of the epitaxy substrate 11 or to the front side 15a of the transfer substrate 15, thereby forming the bonding metal layer 16 having a thickness about 3 μm. Thereafter, the bonding metal layer 16 is brought into pressure contact with the front side 15a of the transfer substrate 15 or the front side 12a of the optical device layer 12, thereby bonding the front side 15a of the transfer substrate 15 through the bonding metal layer 16 to the front side 12a of the optical device layer 12 constituting the optical device wafer 10.

Figure 6:
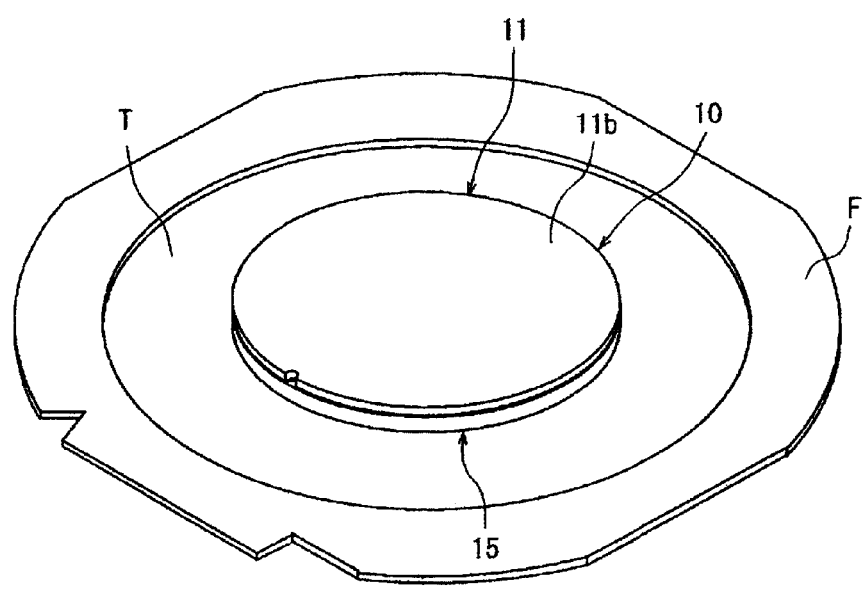
FIG. 6 is a perspective view showing a condition that the transfer substrate bonded to the optical device wafer is attached to a dicing tape supported to an annular frame.

There will now be described a method of setting the power of the laser beam in applying the laser beam from the back side of the epitaxy substrate 11 to the buffer layer 13 by using the laser processing apparatus 1 to thereby peel off the epitaxy substrate 11. In performing the method of setting the power of the laser beam, the transfer substrate 15 bonded to the optical device wafer 10 is attached to the front side (adhesive surface) of a dicing tape T supported to an annular frame F as shown in FIG. 6 (wafer supporting step). Accordingly, the back side 11b of the epitaxy substrate 11 of the optical device wafer 10 is oriented upward in the condition where the unit of the optical device wafer 10 and the transfer substrate 15 is supported through the dicing tape T to the annular frame F.

After performing the wafer supporting step mentioned above, the unit of the optical device wafer 10 and the transfer substrate 15 bonded to the epitaxy substrate 11 supported through the dicing tape T to the annular frame F is placed on the chuck table 36 of the laser processing apparatus 1 shown in FIG. 1 in the condition where the dicing tape T comes into contact with the upper surface of the chuck table 36. By operating the suction means (not shown), the unit of the optical device wafer 10 and the transfer substrate 15 is held under suction through the dicing tape T on the chuck table 36 (wafer holding step). Accordingly, the back side 11b of the epitaxy substrate 11 of the optical device wafer 10 is oriented upward in the condition where the unit of the optical device wafer 10 and the transfer substrate 15 is held under suction through the dicing tape T on the chuck table 36. Further, the annular frame F supporting the dicing tape T is fixed by the clamps 362 provided on the chuck table 36.

Figure 7:
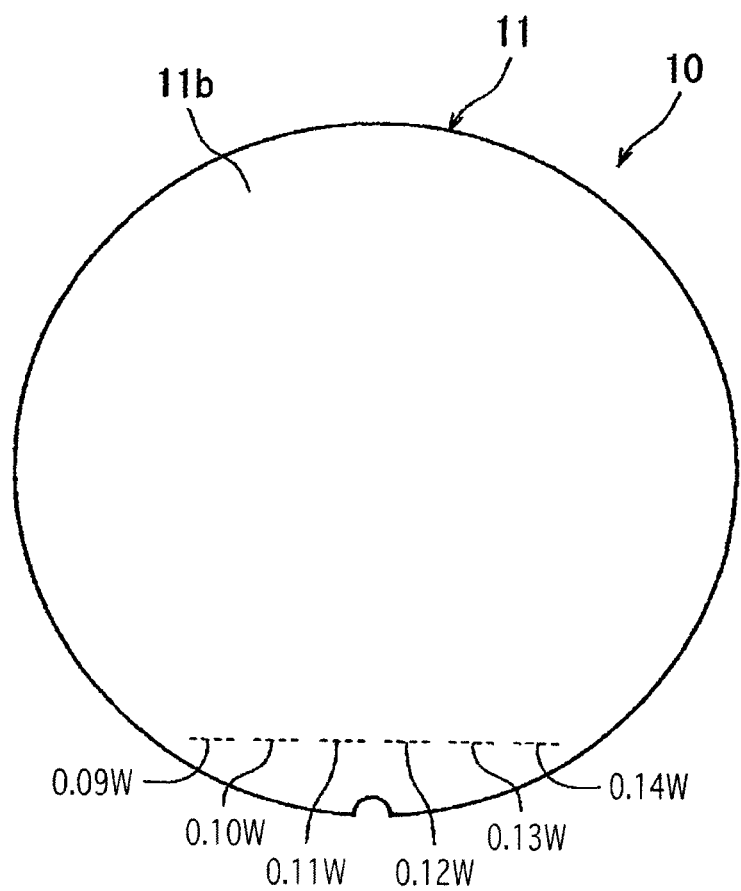
FIG. 7 is a plan view for illustrating a laser beam applying step in the laser beam power setting method according to the present invention.

After performing the wafer holding step mentioned above, the feeding means 37 is operated to move the chuck table 36 to a laser beam applying area below the focusing means 64 of the laser beam applying means 6, thereby positioning a peripheral portion (peripheral marginal area) of the optical device wafer 10 where the optical devices 124 are not formed directly below the focusing means 64. Then, a laser beam applying step is performed in such a manner that the laser beam having a wavelength (257 nm) having transmissivity to sapphire and having absorptivity to gallium nitride (GaN) is applied to the buffer layer 13 from the back side 11b (upper surface) of the epitaxy substrate 11 as changing the power of the laser beam. In this laser beam applying step, the average power of the pulsed laser beam is set to 0.09 W, 0.10 W, 0.11 W, 0.12 W, 0.13 W, and 0.14 W, for example, and the pulsed laser beam is sequentially applied at different positions as shown in FIG. 7. In this preferred embodiment, the repetition frequency of the pulsed laser beam in this laser beam applying step is set to 50 kHz and the pulse width is set to 100 ps. Further, the spot diameter of the pulsed laser beam to be applied from the focusing means 64 onto the upper surface of the buffer layer 13 is set to 70 μm. This spot diameter may be a focused spot diameter or a defocused spot diameter.

Figure 8:
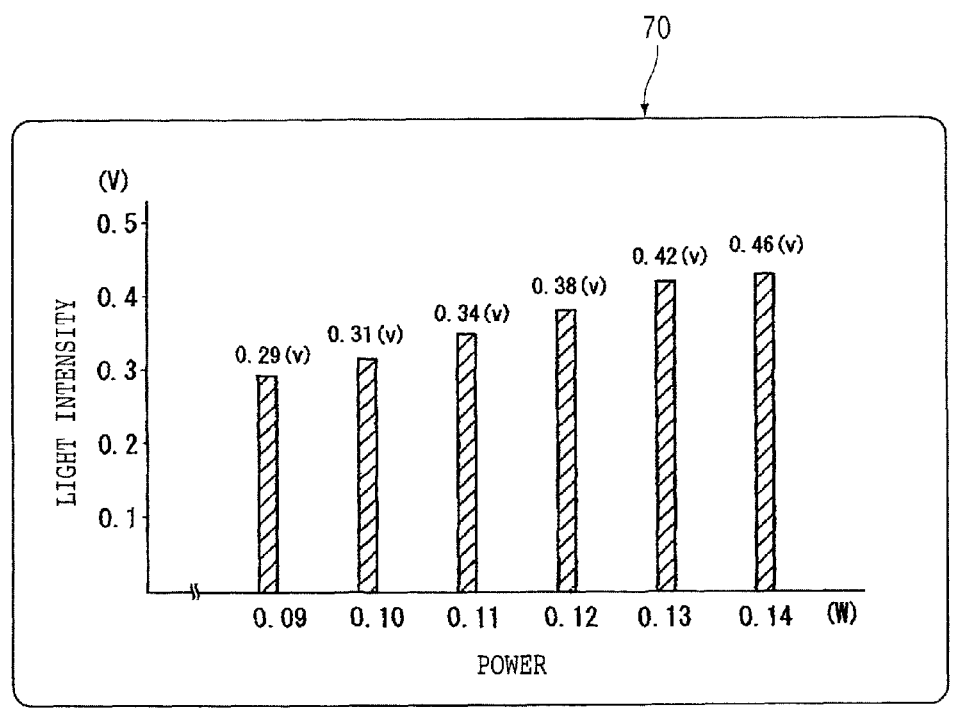
FIG. 8 is a diagram for illustrating a plasma light intensity displaying step in the laser beam power setting method according to the present invention.

During the operation of the laser beam applying step, the control means 7 operates the plasma detecting means 8. Accordingly, the plasma generated by the application of the pulsed laser beam to the buffer layer 13 is guided through the focusing lens 642, the dichroic mirror 81, and the band-pass filter 82 to the photodetector 83, wherein the light having a wavelength region of 400 to 420 nm is detected by the photodetector 83. The photodetector 83 sends a detected light intensity signal as a voltage signal to the control means 7. As shown in FIG. 8, the control means 7 outputs to the display means 70 the light intensities of the plasma corresponding to the different powers of the pulsed laser beam applied to the buffer layer 13 according to the light intensity signal (voltage signal) from the photodetector 83 (plasma light intensity displaying step).

By performing the plasma light intensity displaying step mentioned above, an operator verifies the light intensity of the plasma and the condition of fracture of the buffer layer 13 according to the light intensities of the plasma corresponding to the different powers of the pulsed laser beam applied to the buffer layer 13 as displayed on the display means 70, and sets 0.12 W, for example, as a proper power for reliably decomposing only the buffer layer 13 (power setting step). Then, the operator inputs this proper power of the laser beam (0.12 W in this preferred embodiment) from the input means 71. The control means 7 temporarily stores the input proper power of the laser beam into an internal memory and adjusts the power of the laser beam in a peeling laser beam applying step to be hereinafter described. Further, the operator inputs from the input means 71 the light intensity of the plasma (0.38 V in this preferred embodiment) corresponding to the proper power of the laser beam (0.12 W in this preferred embodiment), and stores this light intensity into the memory of the control means 7. Accordingly, in subsequently processing the same kind of optical device wafers, the power of the laser beam corresponding to the light intensity of the plasma (0.38 V in this preferred embodiment) stored in the memory of the control means 7 can be set as a proper power.

Figure 9A:
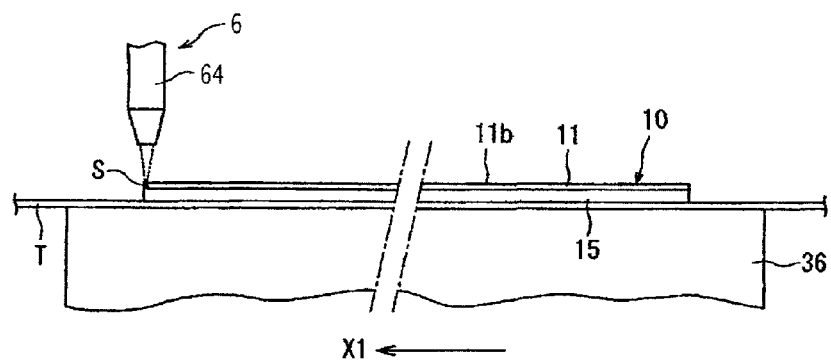
FIGS. 9A to 9C are views for illustrating a peeling laser beam applying step of applying a laser beam to a buffer layer from the back side of an epitaxy substrate constituting the optical device wafer.
Figure 9B:
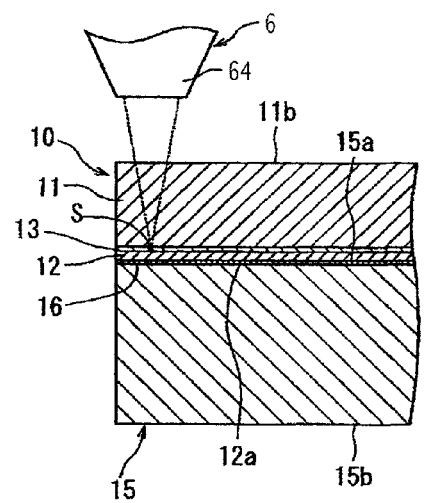

After setting the proper power of the pulsed laser beam (0.12 W in this preferred embodiment) to be applied to the buffer layer 13 as mentioned above, a peeling laser beam applying step is performed in such a manner that the pulsed laser beam having a wavelength having transmissivity to sapphire and having absorptivity to gallium nitride (GaN) is applied to the buffer layer 13 from the back side 11b (upper surface) of the epitaxy substrate 11 as in the laser beam applying step mentioned above in the condition where the average power of the laser beam is set to the above proper power (0.12 W in this preferred embodiment), thereby decomposing (breaking) the buffer layer 13. This peeling laser beam applying step will now be described with reference to FIGS. 9A to 9C. As shown in FIG. 9A, the chuck table 36 is moved to the laser beam applying area below the focusing means 64 of the laser beam applying means 6 so that one end (left end as viewed in FIG. 9A) of the epitaxy substrate 11 is positioned directly below the focusing means 64 of the laser beam applying means 6. Thereafter, the spot diameter of the spot S to be formed on the upper surface of the buffer layer 13 by the pulsed laser beam applied from the focusing means 64 is set to 70 μm. This spot diameter may be a focused spot diameter or a defocused spot diameter as in the laser beam applying step mentioned above.

Figure 9C:
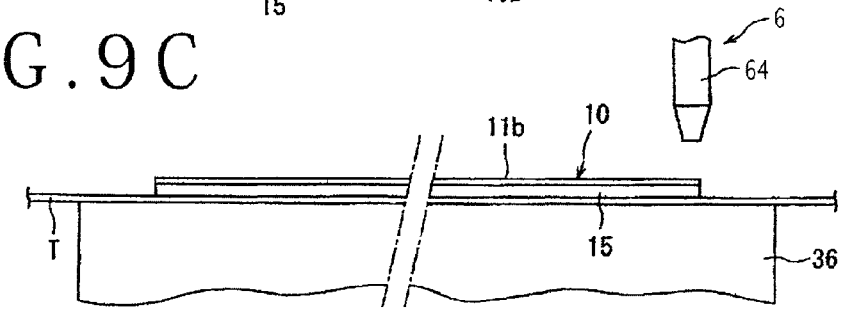

Thereafter, the pulsed laser beam oscillating means 62 is operated and the power adjusting means 63 is controlled to adjust the average power of the pulsed laser beam oscillated by the pulsed laser beam oscillating means 62 to 0.12 W. While the pulsed laser beam is being applied from the focusing means 64, the chuck table 36 is moved in the direction shown by an arrow X1 in FIG. 9A at a predetermined feed speed. When the other end (right end as viewed in FIG. 9C) of the epitaxy substrate 11 reaches the position directly below the focusing means 64 as shown in FIG. 9C, the application of the pulsed laser beam is stopped and the movement of the chuck table 36 is also stopped (peeling laser beam applying step). This peeling laser beam applying step is performed over the entire surface of the buffer layer 13. As a result, the buffer layer 13 is decomposed to lose its binding function of binding the epitaxy substrate 11 and the optical device layer 12.

For example, the peeling laser beam applying step mentioned above is performed under the following processing conditions.

Figure 10:
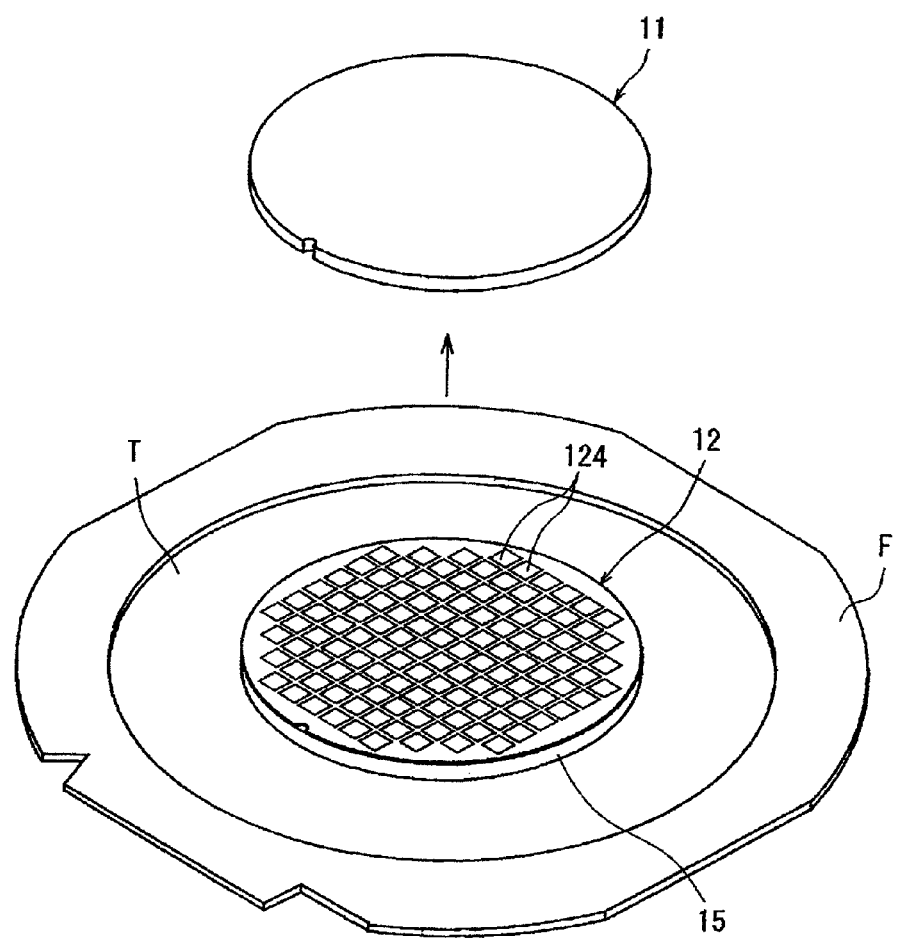
FIG. 10 is a perspective view for illustrating an epitaxy substrate peeling step of peeling off the epitaxy substrate from the optical device layer.

Light source: YAG pulsed laser
Wavelength: 257 nm
Average power: 0.12 W
Repetition frequency: 50 kHz
Pulse width: 100 ps
Spot diameter: 70 μm
Work feed speed: 600 mm/s After performing the peeling laser beam applying step mentioned above, an epitaxy substrate peeling step is performed in such a manner that the epitaxy substrate 11 is peeled off from the optical device layer 12. More specifically, by performing the peeling laser beam applying step, the binding function of the buffer layer 13 binding the epitaxy substrate 11 and the optical device layer 12 is lost. Accordingly, the epitaxy substrate 11 can be easily peeled off from the optical device layer 12 as shown in FIG. 10 (epitaxy substrate peeling step). By peeling off the epitaxy substrate 11 constituting the optical device wafer 10, the optical device layer 12 formed on the front side of the epitaxy substrate 11 is smoothly transferred to the transfer substrate 15.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A laser processing apparatus for removing a sapphire substrate from an optical device wafer configured by forming an optical device layer on a front side of said sapphire substrate through a buffer layer, said laser processing apparatus comprising:

a chuck table for holding said optical device wafer;

laser beam applying means for applying a pulsed laser beam to said optical device wafer held on said chuck table to break said buffer layer, wherein said pulsed laser beam is sequentially set to each of plurality of different powers;

plasma detecting means for detecting the light intensity of plasma light produced in said buffer layer by the application of said pulsed laser beam from said laser beam applying means to said optical device wafer, said plasma detecting means detecting the light intensity of a predetermined wavelength region of said plasma light generated from a substance forming said buffer layer;

a control means for receiving a voltage signal corresponding to the light intensity detected by the plasma detection means and for outputting the voltage signal corresponding to each of said different powers of said pulsed laser beam;

displaying means for displaying said voltage signals corresponding to the light intensity of said plasma light detected by said plasma detecting means such that each of said voltage signals displayed is associated with one of said powers of said pulsed laser beam.

2. The laser processing apparatus according to claim 1, wherein said plasma detecting means comprises:

a dichroic mirror for transmitting said pulsed laser beam applied from said laser beam applying means and reflecting said plasma light produced in said buffer layer, a band-pass filter for passing said predetermined wavelength region of said plasma light generated from said substance forming said buffer layer after said plasma light is reflected by said dichroic mirror, and a photodetector for detecting the light intensity of said plasma light passed through said band-pass filter;

the result of detection by said photodetector being displayed by said displaying means.

* * * * *